United States Patent [19]

Plant et al.

[11] Patent Number: 5,389,523

[45] Date of Patent: Feb. 14, 1995

[54] LIPOSOME IMMUNOANALYSIS BY FLOW INJECTION ASSAY

[75] Inventors: Anne L. Plant, Arlington, Va.; Laurie Locascio-Brown, Silver Spring; Richard A. Durst, Clarksburg, all of Md.

[73] Assignee: The United States of America, as represented by the Secretary of Commerce, Washington, D.C.

[21] Appl. No.: 917,426

[22] Filed: Jul. 23, 1992

Related U.S. Application Data

[63] Continuation of Ser. No. 473,020, Jan. 31, 1990, abandoned, which is a continuation-in-part of Ser. No. 200,210, May 31, 1988, abandoned.

[51] Int. Cl.$^6$ .............. G01N 33/543; G01N 33/544; G01N 33/547; G01N 35/08
[52] U.S. Cl. .................. 435/7.92; 435/7.93; 435/7.94; 435/188; 435/10; 436/518; 436/528; 436/532; 436/541
[58] Field of Search ........... 435/7.92, 7.93, 7.94, 435/188, 810, 961; 436/518, 528, 532, 541, 808, 829

[56] References Cited

U.S. PATENT DOCUMENTS

| | | | |
|---|---|---|---|
| 3,896,217 | 7/1975 | Johnson | 424/1 |
| 4,039,652 | 8/1977 | Adams et al. | 424/1 |
| 4,108,976 | 8/1978 | Reese | 424/1 |
| 4,277,560 | 7/1981 | Gray et al. | 435/7 |
| 4,342,826 | 4/1982 | Cole | 435/7 |
| 4,372,745 | 2/1983 | Mandle et al. | 436/537 |
| 4,397,960 | 8/1983 | Moussebois et al. | 436/512 |
| 4,434,236 | 2/1984 | Freytag | 436/512 |
| 4,444,878 | 4/1984 | Paulus | 435/7 |
| 4,469,787 | 9/1984 | Woods et al. | 435/7 |
| 4,483,929 | 11/1984 | Szoka | 436/533 |
| 4,517,303 | 5/1985 | Freytag et al. | 436/501 |
| 4,551,426 | 11/1985 | Freytag et al. | 435/7 |
| 4,582,810 | 4/1986 | Rosenstein | 436/528 |
| 4,680,120 | 7/1987 | Ramsden et al. | 210/635 |
| 4,704,355 | 11/1987 | Bernstein | 435/6 |
| 4,707,441 | 11/1987 | Ahmad et al. | 435/7 |
| 4,708,933 | 11/1987 | Huang et al. | 435/7 |
| 4,716,121 | 12/1987 | Block et al. | 436/514 |
| 4,743,560 | 5/1988 | Campbell et al. | 436/501 |
| 4,787,075 | 11/1988 | Matsuoka et al. | 369/44 |
| 4,978,625 | 12/1990 | Wagner et al. | 436/518 |

FOREIGN PATENT DOCUMENTS

| | | |
|---|---|---|
| 0276165 | 1/1988 | European Pat. Off. |
| 0302673 | 7/1988 | European Pat. Off. |
| 0284232 | 9/1988 | European Pat. Off. |
| 61-158041 | 7/1986 | Japan . |
| 2014727 | 8/1979 | United Kingdom . |
| WO84/02579 | 7/1984 | WIPO . |
| WO88/06293 | 8/1988 | WIPO . |

OTHER PUBLICATIONS

Schott, H. & B. Leitner "Chromatography of Functionalized Liposomes and their components" J. Chromatography 441:115 1988.

(List continued on next page.)

*Primary Examiner*—Mary E. Ceperley
*Assistant Examiner*—Nancy J. Parsons
*Attorney, Agent, or Firm*—Oliff & Berridge

[57] ABSTRACT

A method of immunoanalysis combines immobilized immunochemistry with the technique of flow injection analysis, and employs microscopic spherical structures called liposomes, or lipid vesicles, as carriers of detectable reagents. Liposomes are modified on their surface with analytical reagents, and carry in their internal volume a very large number of fluorescent or electroactive molecules. Aspects of this embodiment of the invention include the chemistry for covalent immobilization of antibody fragments in a specified orientation, the use of liposomes in a flow injection analysis system, and the combination of automated sampling and analysis with reusable immunoreactants. Another aspect of the invention involves the non-covalent binding of liposomes to a receptor for use in a homogeneous assay. In another aspect of the invention the intensity of scattered light is quantitated as a measure of liposome aggregation in response to a concentration-dependent immunospecific reaction.

28 Claims, 9 Drawing Sheets

OTHER PUBLICATIONS

Locascio-Brown et al., "Behavior of Liposomes in Flow Injection Systems", Analytical Chemistry, Apr. 15, 1988, pp. 792–797.

Plant et al., "Generic Liposome Reagent for Immunoassays", Jun. 23, 1988, Analytical Biochemistry, pp. 001–007.

Sportsman et al., "Chromatographic Properties of Silica-Immobilized Antibodies", Anal. Chem., 1980, 52, 2013–2018.

W. Uditha de Alwis et al., "Rapid Sub-Picomole Electrochemical Enzyme Immunoassay for Immunoglobulin G", Anal. Chem., 1985, 57, 2754–2756.

Sportsman et al., "Kinetic and Equilibrium Studies of Insulin Immunoaffinity Chromatography" Anal. Chem. 1983, 55, 771–775.

Locascio-Brown et al., "Behavior of Liposomes in Flow Injection Systems", *Analytical Chemistry*, Apr. 15, 1988, pp. 792–797.

Harrow et al., "Heterogeneous Samples in Flow-Injection Systems", *Analytica Chimica Acta.*, 174 (1985) pp. 115–122.

FIA ASSAY SCHEMES

- GLASS BEAD W/F(AB)
- LIP-AG
- ANALYTE
- LIP-AB

COMPETITIVE ASSAYS

FILTER TO REMOVE INTERFERING SUBSTANCES

NON-COMPETITIVE ASSAYS

WASTE
CAN APPLY LARGE SAMPLE VOLUME (SANDWICH ASSAY)

LIPOSOME IMMUNOANALYSIS BY FLOW INJECTION ASSAY

This application is a continuation of application Ser. No. 07/473,020, filed Jan. 31, 1990, (abandoned) which in turn is a continuation-in-part of application Ser. No. 200,210, filed May 31, 1988, (abandoned).

BACKGROUND OF THE INVENTION

Antigen-antibody interactions are the basis of sensitive diagnostic techniques such as radioimmunoassay (RIA) and enzyme-linked immunosorbent assay (ELISA). Although these techniques are very sensitive and widely used, they are time-consuming and technically cumbersome. Commercial antibody-based diagnostic kits for hormone and drug detection are easier to use; some of these are disposable single-use devices that are semi-quantitative and permit direct observation of color changes. Such devices cannot be calibrated, however, which limits their analytical potential. A research approach currently being studied by a group headed by George Wilson at the University of Kansas employs immobilized antibodies in liquid chromatographic systems. In short, there are a very large number of configurations possible for immuno-based devices but for credible analytical applications, the optimal immuno-based assay system should be fast, reliable, sensitive, quantitative, reusable, and automated.

One approach to developing such a system involves the use of liposomes in a flow injection immunoassay.

Flow injection immunoanalysis (FIIA) is an analytical approach to immunoassays which combines immunochemistry with the technique of flow injection analysis (FIA). FIA is a continuous-flow method based on the introduction of a sample aliquot into a moving non-segmented carrier stream. Introductions and directions of flow may be determined by a series of microprocessor-controlled solenoid valves.

Immunoassays are of great importance because of their specificity toward analytes present in complex mixtures, and their high sensitivity. Most immunoassays involve the use of a fluorescent or chemiluminescent, enzyme, or radioactive label on an immunoreactive species which serves as an indicator that an immunospecific reaction has occurred. Such immunoassays are discussed in U.S. Pat. Nos. 4,372,745; 4,551,426; and 4,108,976. Immunoassays can be divided into two broad categories, heterogeneous (solid phase) assays and homogeneous (solution phase) assays. Heterogeneous immunoassays have been developed which use the three types of labels previously mentioned. Certain fluorescent and enzyme tags are also used in homogeneous immunoassays, but these uses are limited to small ligands.

Enzyme-linked immunosorbant assays (ELISAs) involve the use of an enzyme covalently coupled to an immunoreactive reagent to serve as an indicator that an immunospecific reaction has occurred. The enzyme is linked to a secondary reagent, which is added to the assay after the initial immunochemical interaction between the analyte or ligand and the antibody. The sensitivity of ELISA is due to the number of turnover events the enzyme is capable of during an incubation period with a substrate that is cleaved to a colored product. While ELISA can be extremely sensitive, it is frequently a very time-consuming assay.

Uses for liposomes in immunoassays have been developed. Liposomes are spherical membrane structures which form spontaneously when phospholipid molecules are dispersed in water. The bilayer membranes of liposomes are similar to cellular membranes and surround an entrapped aqueous volume. Markers, such as water-soluble fluorescent molecules, such as the dye carboxyfluorescein, or electroactive markers, such as potassium ferrocyanide, are trapped inside the lipid membrane, and non-trapped material is removed from the outside of the structures by gel filtration. There are a number of methods established for liposome preparation. Liposomes prepared having a bilayer thickness of 40 angstroms, at higher concentrations, may contain approximately $1 \times 10^5$ carboxyfluorescein molecules within.

The detection of binding of antigen analytes to antibodies may be accomplished by the use of radioactive or fluorophore- or enzyme- tagged molecules. Modification usually involves one to several fluorophores per molecule or one enzyme which is capable of several hundred turnover events in a reasonable period of time. Radioactivity is more sensitive, since many decay events can be counted, but there are many disadvantages to radio labels. Labeling analyte analogs or ligand binding proteins such as antibodies with liposomes containing fluoroescent or electro-active molecules is analogous to labeling these agents with radioisotopes or enzymes. The advantage of liposomes is that they provide real-time detectability of up to $1 \times 10^5$ entrapped molecules for every molecule event they are associated with. The use of liposomes provides as much sensitivity as radio labels but is safer, faster and more convenient. Some preparations are extremely stable, with no aggregating and no detectable change in size or other characteristics after storage for years.

Some assays take place in solution, and involve immunospecific lysis of liposomes in the presence of interacting immunochemical species, one of which is the desired analyte, and a complex biologically derived lytic reagent called complement. These assays are discussed in U.S. Pat. Nos. 4,707,441 and 4,483,929. A solid-phase liposome immunoassay which involves immunospecific disruption of liposomes is discussed in U.S. Pat. No. 4,708,933.

U.S. Pat. No. 4,708,933 discloses an immunoliposome assay wherein liposomes are modified to contain antigen and dye. When these liposomes come into contact with an inert solid surface having antibody molecules attached thereto, rapid binding occurs between the antigen-lipid complex and the antibody, disrupting the liposome and releasing the dye which can be quantitatively measured.

Liposomes can also be used in homogeneous assays. These assays involve incorporating fluorophores or enzymes into liposomes, and modulating the detectable signal as a result of an immunospecific response. In this case, the immunospecific response requires the presence of interacting immunochemical species, one of which is the desired analyte, and a complex biologically derived lytic reagent called complement. Such assays are discussed in U.S. Pat. Nos. 4,707,441 and 4,483,929. Some immunoassays are based on the immunospecific aggregation of latex particles. Latex particles must be covalently derivatized with immunoreactive reagents, and the stability of latex particles after long-term storage is a problem. A need arises for an immunoassay which overcomes these problems.

SUMMARY OF THE INVENTION

It is an object of the present invention to combine the use of liposomes in an immunoanalysis method with a flow injection analysis system.

It is a further object of the present invention to prepare liposomes as immunoreactants by noncovalent coupling of biotinylated binding agent with biotinylated liposomal lipids through the protein, avidin.

It is a further object of the present invention to covalently immobilize antibody fragments in a special orientation to develop an accurate and efficient immunoanalysis method.

It is yet a further object of the present invention to combine automated sampling and analysis with reusable immuno-reactants.

In one aspect, the present invention is directed to a method of immunoanalysis which combines immobilized immunochemistry with the technique of flow injection analysis, and employs microscopic liposomes as carriers of detectable reagents. Liposomes are modified on their surface with analytical reagents, and carry in their internal volume a large number of detectable marker molecules. The modified liposomes can bind to antibody fragments immobilized on an immunoreactor column. Liposomes left unbound, due to the presence of an analyte in a competitive assay, can be lysed and the marker component concentration detected. This results in a quantification of the concentration of the analyte. Non-competitive assays can also be performed using the liposomes.

Another embodiment of the present invention relates to binding assays involving modified liposomes whose marker compound can be quantified at a later step in the assay directly, or by disrupting or lysing the liposomes. The amount of the marker compound released can then be related to the concentration of analyte in the sample being tested. Similar assays may be performed manually, without the use of flow injection analysis and are contemplated as equivalents within the scope of this invention.

The present invention also relates to a liposome immunoassay which involves incorporating fluorophores into liposomes, and modifying the liposome membrane with an immunoreactive reagent. The present invention also covers another use for liposomes in a homogeneous assay wherein liposomes are noncovalently derivatized using methods generic to all immunoreactive reagents.

In another embodiment of the present invention, the intensity of scattered light is quantitated as a measure of liposome aggregation in response to a concentration-dependent immunospecific reaction. In this embodiment, encapsulation of marker molecules into liposomes is not required.

The present invention also relates to assays for the purpose of diagnostics and rapid detection and quantitation. The simplicity of the techniques, and the fact that they are relatively rapid, make them very applicable to low-technology environments, which may include physician's offices, or walk-in clinics. For the same reasons, it will have application to field use, such as for testing of water purity.

The invention may be more fully understood with reference to the accompanying drawings and the following description of the embodiments both discussed herein and shown in those drawings. The invention should be recognized as contemplating all modifications within the skill of an ordinary artisan.

DESCRIPTION OF PREFERRED EMBODIMENTS

Immobilization of antibodies which bind an analyte of interest in a FIIA reactor is the first step in developing a reusable, automated immunoanalyzer. Noncovalent association of antibodies with glass or plastic surfaces is the immobilization technique commonly used for many ELISA and RIA assays. In the process of binding during assays of this type, many potential antibody binding sites are blocked, activity is lost, and precise quantification of number and affinity of remaining sites is not known, resulting in a concomitant loss of analytical accuracy. The most frequently used chemistry for covalent immobilization is through amine groups of the antibody protein, of which there are many. The random selection of reactive groups leads again to loss of activity when amines near the binding site are involved.

In one embodiment, phospholipid molecules derivatized with antigen are inserted into the membrane of each liposome. The modified liposomes can compete with analyte molecules in a sample for binding to immobilized antibody fragments on an immunoreactor column. Liposomes are selected which will not disrupt upon binding to a solid phase support, e.g., upon binding between a binding agent incorporated into the surface membrane of a liposome and a receptor on a solid phase support. As a result, for every liposome not bound to the column, $1 \times 10^5$ molecules of marker compound are available for detection and quantification. Non-competitive assays can also be performed using derivatized liposomes and, inter alia, sandwich-type assay schemes. Automated sampling and analysis can be combined with reusable immunoreactants when regeneration of the immunoreactor is performed. The invention is also directed to products useful in said assay, especially in kit form.

Figure 1:
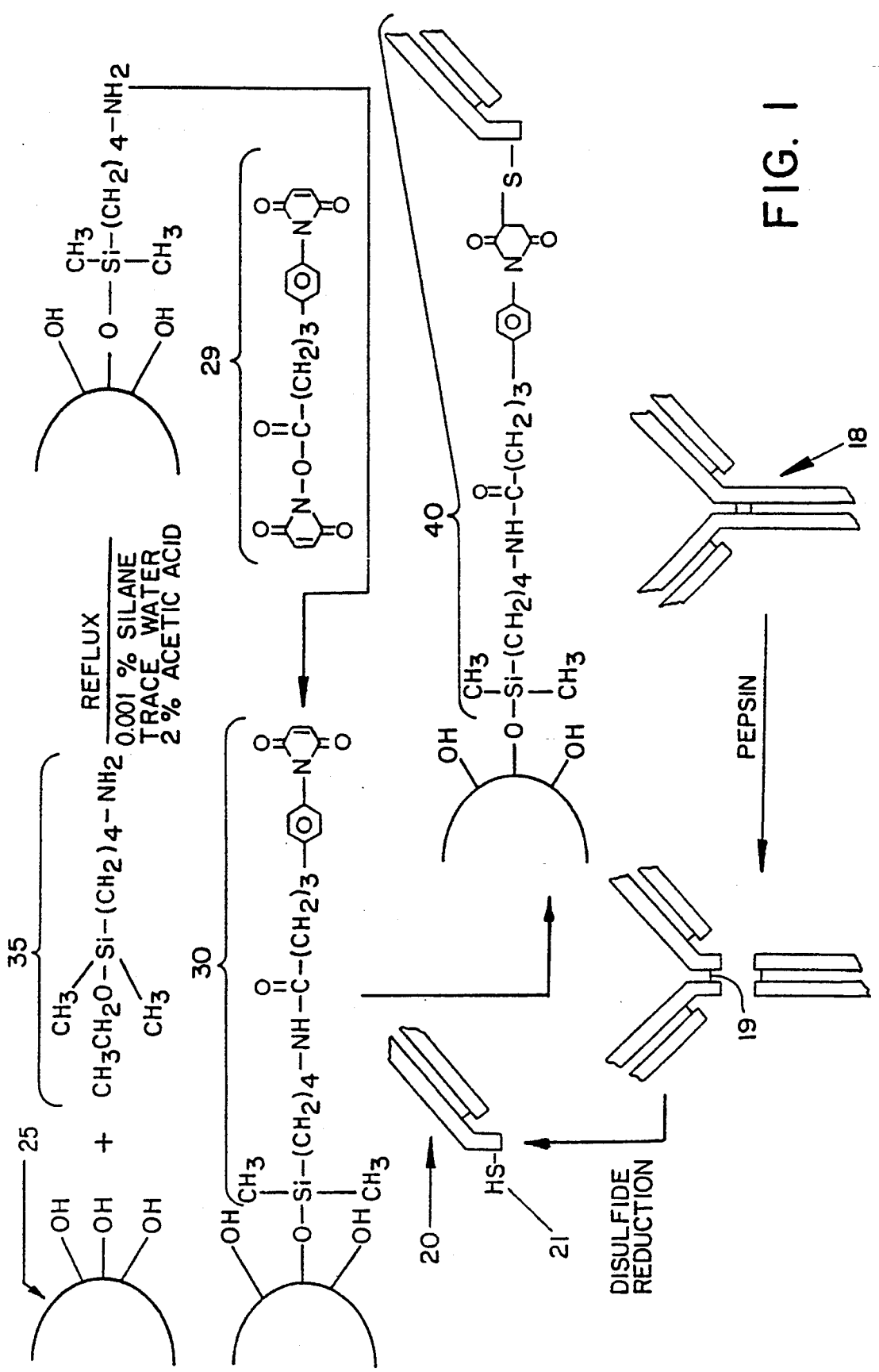
FIG. 1 illustrates a method of immobilizing the antigen binding portion of antibodies.

According to an important embodiment of the present invention, the antibody 18 is cleaved by the enzyme pepsin, and the disulfide bridge 19 at the "hinge" region of the resulting fragment is then chemically reduced to sulfhydryl groups. The antigen-binding portion 20 of antibodies 18, the Fab' fragments, are immobilized through their sulfhydryl groups 21 to glass 25 via a derivatized silane linkage 30 (FIG. 1). The sulfhydryl group is used for covalent attachment to the silane 35 via the bifunctional linking agent, succinimidyl-4-(p-maleimidophenyl)-butyrate 29. The resulting orientation of the fragment with respect to the glass bead solid phase preserves the reactivity of the antigen-binding site. The advantage to this approach is three-fold. First, almost 100% of oriented immobilized antibody is active, in contrast to the 10 or 20% activity seen after noncovalent immobilization. This conserves expensive antibody not only in the initial solid phase preparation step, but also produces a reactive surface which is reusable. Second, the number of active antibody molecules which are covalently immobilized can be determined, allowing quantitative prediction of column activity. The third advantage derives from the fact that the preparation of non-covalently derivatized solid phases by nonspecific adsorption of antibody is frequently the most time-consuming step in ELISA-type assays. The ability to prepare stable, covalently immobilized antibodies which can be stored and reused greatly improves the time required to perform an assay.

Referring to FIG. 1, the immunoreactor is prepared by immobilizing, on the column packing material, the antigen-binding portion of antibodies, the Fab' fragments 20, through their sulfhydryl groups 21 to glass 25 via a silane linkage 30. The silane reagent 35 depicted is 4-amino-butyldimethyl ethoxysilane, although any silane which can be derivatized to a primary amine group can be used. Under reflux, the silane reagent 35 binds to the glass beads 25. The bifunctional linking agent 29 is then added and binds to the primary amine of the silane 35. The completed silane linkage 30 immobilizes the Fab' fragments 20 through their sulfhydryl groups 21. As a result, the covalently bonded complete antigen-binding site linkage 40 provides almost 100% activity of the immobilized antibodies. Alternatively, polystyrene is derivatized with amino groups by successive oxidation and reduction reactions. The modified polystyrene must be stable at pH 7 or 8 in aqueous conditions, and withstand treatment with various chaotropic agents, such as alcohols or glycine-HCl at pH 2, that are required for regeneration of analyte binding sites. Alternatively, intact molecules can be immobilized onto silicious or polystyrene surfaces using other chemistries.

Figure 2:
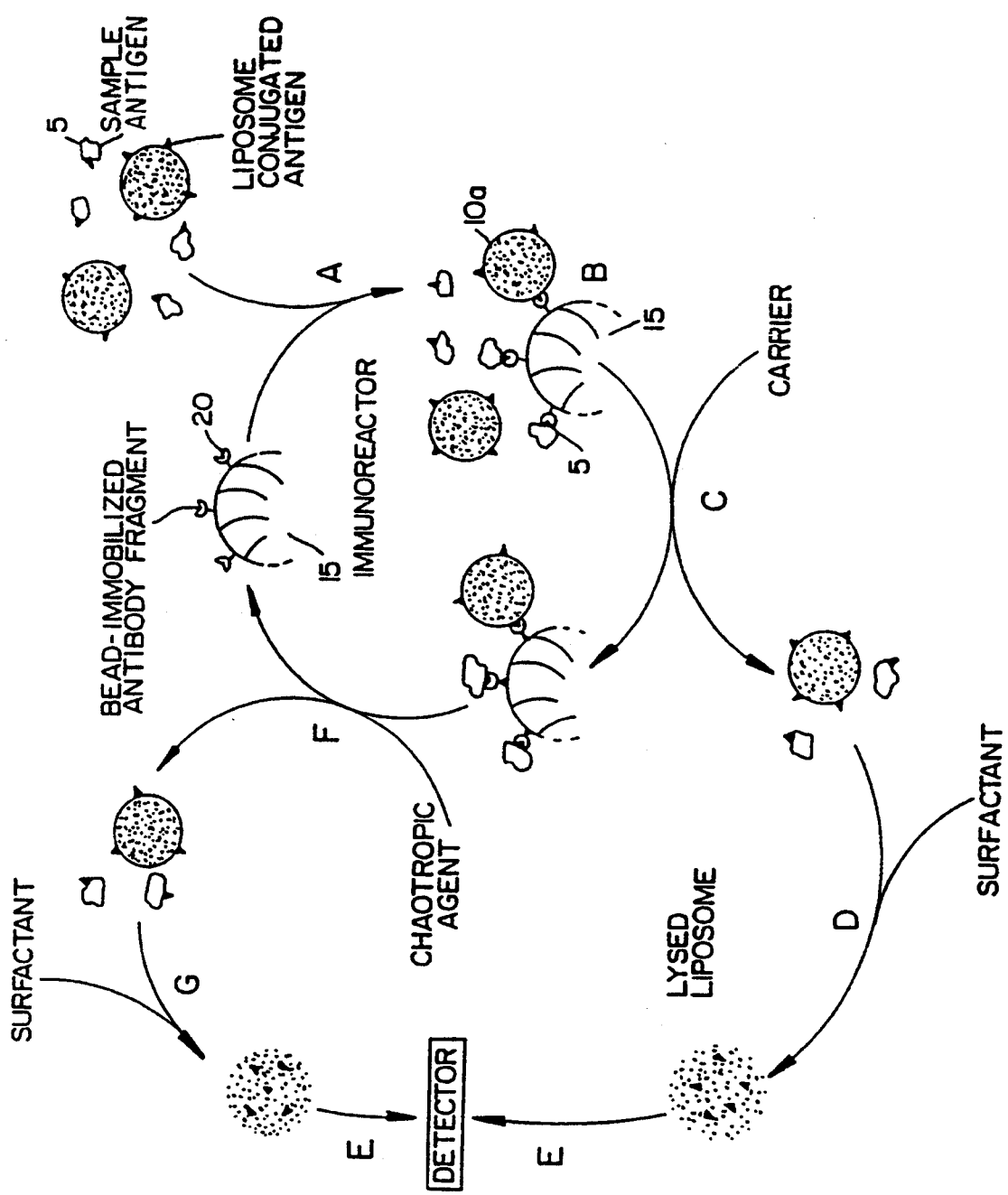
FIG. 2 is a schematic representation of the solid-state immunoliposome assay of the present invention.

As shown in FIG. 2, when an analytical sample containing the compound of interest is injected into the FIIA system, interactions between analyte antigens 5 and the immobilized antibody fragments 20 occur on the surface of the beads 15 in the immunoreactor column. Detection of this interaction is mediated through the use of sensitized liposomes.

Liposomes 10a can compete for binding to immobilized antibodies 20 in the immunoreactor column with analyte molecules 5 in a sample; then for every liposome 10a which does not bind to the column 15 due to the presence of an analyte molecule 5, approximately $1 \times 10^5$ marker (e.g., fluorescent) molecules are available for detection. Phospholipid molecules derivatized with antigen, antibody, Fab' fragments or class-specific binding agent are inserted into the membrane of each liposome. Alternatively, liposomes can be derivatized with virtually any molecule, hereforth referred to as a binding agent, in the following manner: phospholipid molecules derivatized with the vitamin biotin are inserted into the liposome membranes. The protein avidin, which has several binding sites for biotin, is added, and binds strongly to the biotin molecules on the liposomes. Then, a binding agent which is derivatized with biotin is added, and binds to avidin on the liposomes. These sensitized liposomes, which display binding agents on their surface, can now bind to antibody fragments on the solid support of the immunoreactor column or to other binding agents.

Liposomes can be noncovalently derivatized on their surfaces with virtually any analytical reagent. The interaction of biotinylated antigens or antibodies with liposomes containing biotinylphosphatidylethanolamine in the presence of avidin is so strong that it is as effective as a covalent bond.

In the competitive binding scheme shown in FIG. 2, a sample and liposome reagent are injected into the system (step A). At the reactor, competitive binding occurs (step B). The number of liposomes which do not bind to antibody on the reactor are carried downstream (step C) where they can be detected, or, if they contain quenched fluorophore or electroactive molecules, they can enter a post-column mixing chamber. Here, surfactant is added (step D) which disrupts the membrane of liposomes, releasing their aqueous fluorescent or electroactive contents which pass into the detector (step E). Thus, for every liposome excluded from the column due to the binding of an analyte molecule, approximately $10^5$ detectable molecules are released. The reactor is regenerated (step F) by disrupting the liposomes, and subsequently the interaction of binding agent or analyte and immobilized antibody, and a new sample can be injected (step A). In addition, the quantity of liposome marker molecules released in step F can also be subsequently determined (scheme II of FIG. 4).

Different methods for the detection and quantification of marker compounds allow diverse applications of immunoassay methods. When using liposomes containing enzymes as marker compounds in their interior phase, disruption of the liposomes can allow the released enzymes to form enzyme reaction products which are more detectable than the enzymes themselves as marker compounds. This provides a further amplification of the detectability of the marker compounds. Color dyes may also be used as detectable marker compounds and in some cases do not require rupturing of the liposomes for detection and measuring.

The detectability of fluorophores in fluorescent marker compounds can also be accomplished by various methods. In one embodiment of the present invention, unquenched fluorophore marker compounds in the interior aqueous phase of sensitized liposomes can be detected with or without disrupting the liposomes. In another embodiment, quenched fluorophores from the interior aqueous phase of sensitized liposomes are detected after disruption of the liposomes results in unquenching of those fluorophores. Quenching characteristics of various fluorophores can be controlled by concentration gradients as well as other physical and chemical properties of the system.

Figure 3:
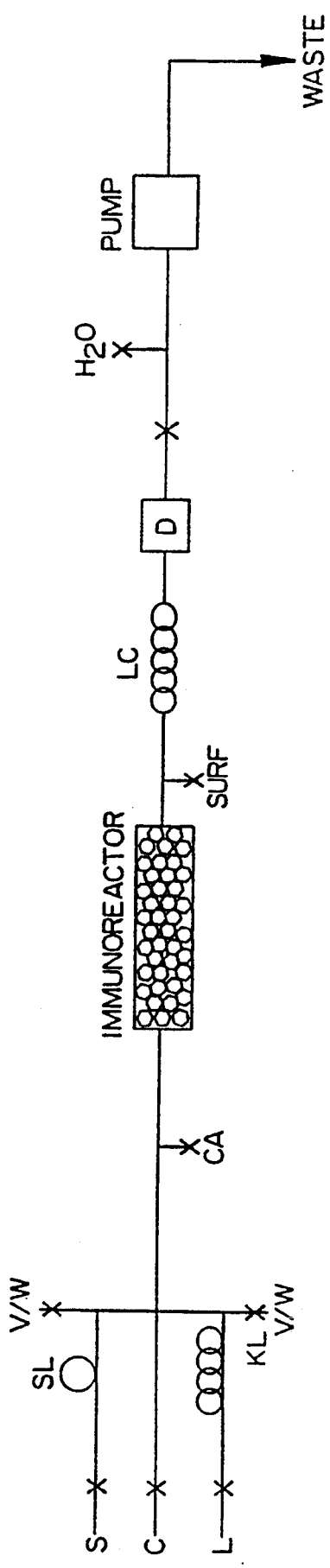
FIG. 3 is a schematic diagram of a flow injection immunoanalysis system of the present invention.

A schematic of one prototype FIIA system is shown in FIG. 3. The system operates under low-pressure and low flow-rates, and is simple and inexpensive to build. Microprocessor-controlled solenoid pinch valves X and tubing are rated to pressures of up to 2.1 bar. A sample solution S is aspirated into a sample injection loop SL using a vacuum V/W with a negative pressure of 0.03 bar. The vacuum may lead to a waste disposal at a system outlet. Because the sequence and timing of events are microprocessor-controlled, injections are precise and reproducible. The rate of flow is typically 0.5 ml min$^{-1}$, controlled with a 4-channel peristaltic pump which may also be placed at an outlet of the system. The analyte-containing sample S is injected into sample loop SL and sensitized liposomes L are injected into sample loop KL which is appropriately coiled or knotted to promote mixing. The immunoreactor column is typically a glass column packed with nonporous soda lime glass beads or with solid polystyrene spheres which range from 100 to several hundred micrometers in diameter and may be derivatized as described above. As the injected sample S is transported through the system, it undergoes controlled dispersion and can interact with immobilized reagent on the immunoreactor column. The sample may also be chemically and/or physically treated by the introduction of appropriate reagents or processing such as mixing with a carrier solution C and/or chaotropic agents CA. The result of this sample treatment is then quantified, preferably by using a surfactant Surf to disrupt the liposomes L, a lysis delay coil LC to promote complete disruption, and a fluorescence or electrochemical flow-through detector D to detect marker compound released by the disrupted liposomes.

Figure 4:
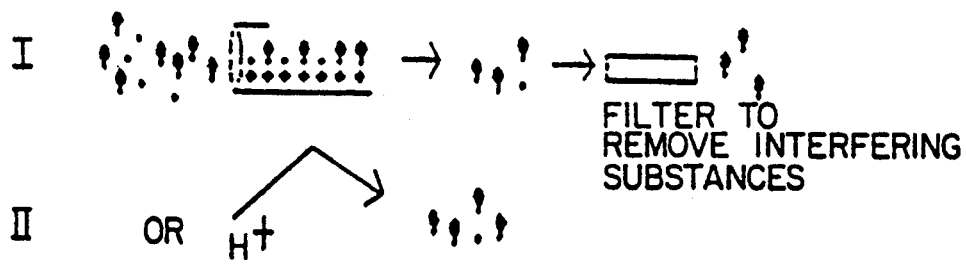
FIG. 4 is a schematic representation of flow injection analysis assays of the present invention.
Figure 4:
Figure 4:
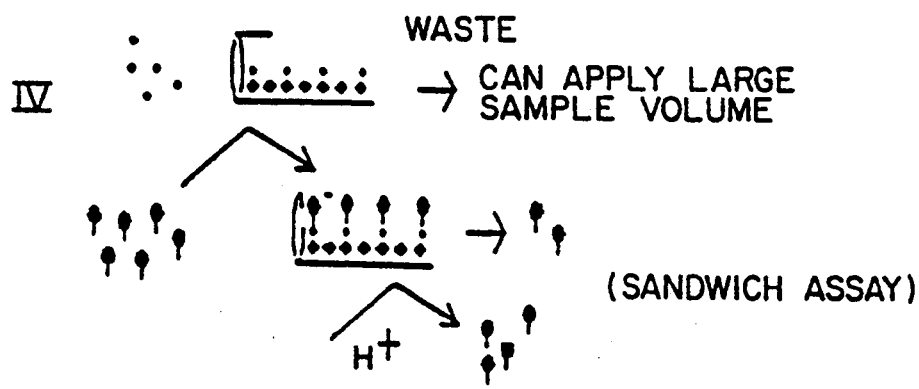
Figure 4:
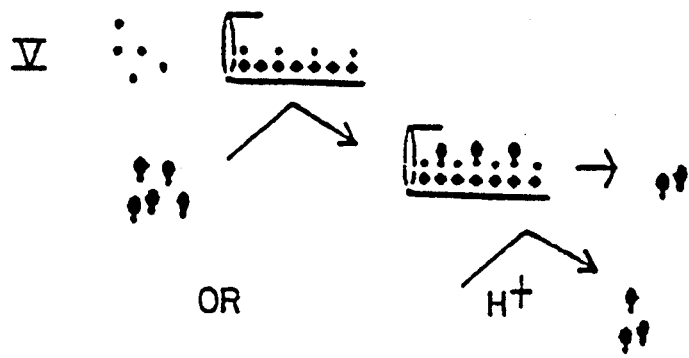

The FIA configuration is readily adaptable to different immunoassay formats, including noncompetitive assays (FIG. 4 assays III–V). Adapting the system to a new analyte is straightforward since the chemistry for antibody fragment immobilization is generic. Once prepared, an immunoreactor column specific for a particular analyte is expected to be stable to storage for many months, and reusable for hundreds of assays. The system can be adapted to quantify more than one analyte simultaneously. The use of microprocessor control allows completely automated operation. FIA is a multi-sampling, high throughput technique based on small reaction volumes. The small volume reactor column produces rapid equilibration times for antigen-antibody reactions, in sharp contrast to the lengthy adsorption steps required for most solid-phase assays. Because reagents are immobilized, the system is reusable and expensive reagents are conserved. In addition, the ability to reuse the immunoreactor column means that the system can be calibrated with known solutions and provide quantitative information, in contrast to the qualitative or semiquantitative response of current assays.

FIG. 4 illustrates different competitive and non-competitive FIA assay schemes according to an embodiment of the present invention.

The competitive assays, schemes I and II, are based on there being a limited number of sites available for binding the antigen-derivatized liposomes and analytes to the Fab' receptors on the immunoreactor column.

Scheme I illustrates the saturation of the reactor with both a liposome reagent and a sample. If the binding of the analyte to the reactor receptors results in fewer receptor sites available for binding than the number of derivatized liposomes in the reactor, then the number of liposomes not bound to the receptor can be related to the number of analytes bound. The concentration of analyte in the sample reagent can thus be determined by detecting the number of unbound liposomes.

Scheme II also illustrates saturating the reactor with both a liposome reagent and a sample reagent, but, unlike scheme I, the number of bound liposomes are detected and can be related to the number of analyte molecules bound to the reactor. An acid, detergent or solvent is used to wash the bound liposomes from the reactor so they can be detected and quantified.

Preferred non-competitive assays according to present invention are illustrated by schemes III–V in FIG. 4.

Scheme III represents a non-competitive assay employing liposomes derivatized with whole antibodies or the antigen-binding portion, Fab' fragments, of antibodies in their outer membranes. An excess of derivatized liposomes is mixed with a sample, and the Fab' portions of the liposomes react with and bind to the analytes in the sample. This mixture is then introduced into the reactor where binding of unreacted liposomes takes place. The reactor, according to this scheme, has been covalently derivatized with an appropriate binding agent, which is an analyte analog, prior to introducing the liposome-sample mixture. The liposomes not bound to sample analytes can bind to the binding agents on the reactor. Liposomes bound to sample analytes do not bind to the reactor and thus pass through the reactor and downstream where they can be collected and quantified. The number of liposomes collected is thus directly related to the number of analyte molecules in the sample.

Scheme IV is a sandwich-type assay which, like scheme III, employs liposomes derivatized with antibodies or with the Fab' fragments of antibodies in their outer membranes. The reactor receptors are also antibodies or Fab' fragments. Here, the sample reagent is first introduced into the reactor where binding between the analytes and the reactor receptors takes place. The reactor is then saturated with the derivatized liposomes which bind to the analytes already bound to the reactor. Remaining liposomes do not bind to the reactor receptor but are instead carried downstream. The number of liposomes bound to the reactor is thus directly proportional to the number of analyte molecules in the sample. The bound liposomes can also be liberated by washing the reactor with a regenerating agent and collecting and quantifying the markers downstream.

Scheme V of FIG. 4 is yet another non-competitive assay of the present invention. Here, the sample reagent is first introduced into the reactor where the analytes bind to the reactor receptors. Then, liposomes sensitized with antigens in their outer membranes are introduced into the reactor where they bind to the remaining unbound reactor receptor sites. The difference between the number of liposomes not bound and the number of liposomes introduced into the reactor is related to the number of reactor receptor sites not bound to analyte molecules. Alternatively, the reactor column can be washed with a regenerating agent to free the liposome marker molecules so they can be collected and quantified downstream. The number of marker molecules can be related to the number of analyte molecules bound to the reactor.

This invention is useful for quantification of analytes which could be antigens or antibodies, such as might be found in clinical samples or in large scale fermentation reactions. Operation modes include sequential automated injection of specimens, or on-line monitoring at designated time intervals. It could be used as well for quantification of particulate infectious agents such as viruses and bacteria, and for detection and separation of cells according to their surface antigens. Continuous effluent stream monitoring is also possible with few modifications to the current design.

The present application also relates to a liposome-linked immunosorbant assay which uses liposomes for the detection and quantitation of interacting species with receptors which can be noncovalently immobilized in a format which can be performed manually. The invention also relates to a liposome aggregation immunoassay wherein aggregation of liposomes in solution is detected by an increase in the intensity of light scattered by the solution which is used to determine the concentration of immunoreactive chemicals present in the solution. In this case, liposomes would not have to contain marker molecules, and the assay would be performed in the homogeneous phase by an automated or non-automated method. In another embodiment of the present invention, a manual immunoassay is provided where immobilized antibody is exposed to liposomes containing a visible dye.

Figure 5:
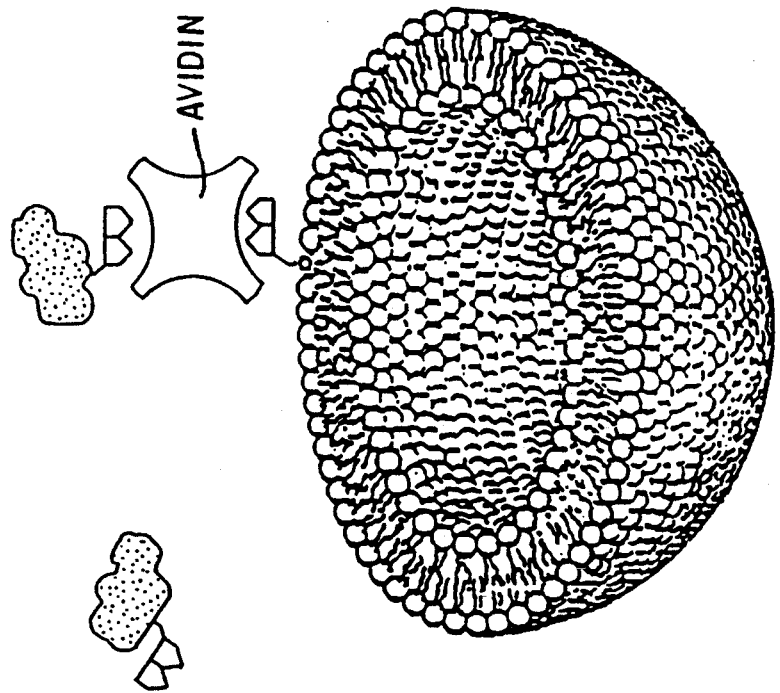
FIG. 5 is a schematic diagram showing derivatization of liposomes prepared for use in the present invention.
Figure 5:
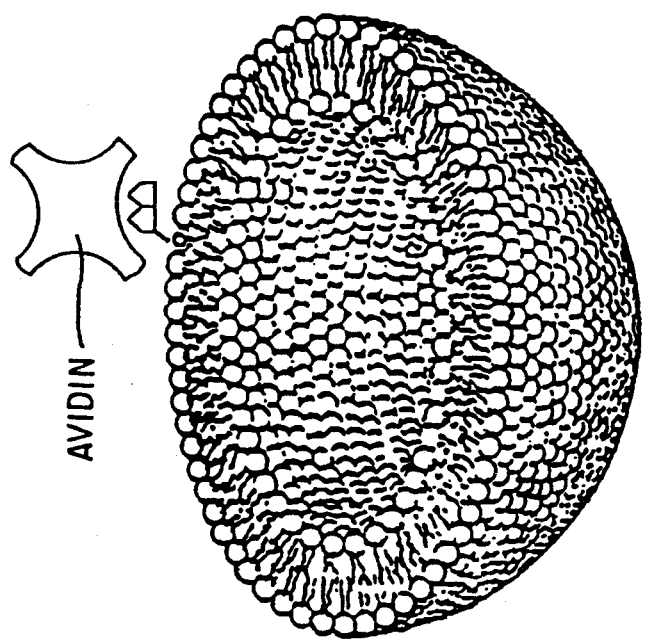

In the following immunoassays of the present invention, liposomes were prepared by an injection method from a lipid mixture of dimyristoylphosphatidylcholine (Avanti Polar lipids, Birmingham, Ala.), cholesterol and dicetylphosphate (Sigma Chemicals, St. Louis, Mo.) at a molar ratio of 5:4:1. Varying amounts of N-biotinoyldipalmitoyl-L-phosphatidylethanolamine (B-PE) (Molecular Probes, Junction City, Oreg.) were added to this mixture to achieve concentrations of 0.01 to 1 mol % of total lipid. To prepare liposomes, 2 mol stock lipid mixture in chloroform were evaporated under a stream of nitrogen, and then placed in a vacuum desiccator overnight. The lipid was resolubilized in 0.05 ml of dry isopropanol, and injected with a syringe into 1 ml buffer which was being mixed by vortex. For assays using fluorescent liposomes, this buffer contained the fluorophore, carboxyfluorescein. For assays using a visible dye, the buffer contains dye. Liposomes of uniform size are formed spontaneously by this method. Different methods of preparation can be used, and variation in lipid components is possible. In this case, liposomes are prepared with B-PE so that they can be derivatized noncovalently with biotinylated antibodies or ligands, using avidin as a crosslink. A schematic of this method of derivatization of liposomes is shown in FIG. 5.

To derivatize liposomes, avidin was added to a small volume of liposomes at a concentration to provide a B-PE:avidin molar ratio of 5, and after 2 min, biotinylantitheophylline was added at a molar ratio of antibody:avidin 3. A schematic of this method is shown in FIG. 5.

For the liposome immunosorbant assay (LISA) and the analogous ELISA, liposomes were prepared as above with the B-PE being added to the initial mixture at a concentration of 0.1 mol % of total lipid. Bovine serum albumin (BSA) was covalently coupled to aminopropyl theophylline analog supplied by IGEN, Inc. (Rockville, Md.) with bis(sulfosuccinimidylsuberate) (Pierce Chemical Company, Rockford, Ill.). Monoclonal antitheophylline antibody purchased from American Qualex (La Mirada, Calif.) was purified from ascites fluid with Protein A. Purified antitheophylline was biotinylated with N-hydroxysuccinimidobiotin (NHS-biotin from Pierce) in the following procedure. A 100-fold molar excess of NHS-biotin in DMSO was added to antibody in phosphate-buffered saline (PBS), pH 7.2, and stirred at room temperature for 2 hr., followed by dialysis against PBS. Antitheophylline was noncovalently conjugated to liposomes containing carboxyfluorescein.

The ELISA and LISA assays were based on binding of antitheophylline antibody or antitheophylline-liposomes to theophylline-BSA conjugate which was nonspecifically adsorbed to a plastic support. ELISA was performed in 96-well microtiter plates, and for LISA, disposable polystyrene cuvettes were used. Varying concentrations of theophylline were added to wells and cuvettes to compete for binding to antitheophylline or antitheophylline liposomes. The amount of signal for both the ELISA and the LISA was inversely related to the amount of theophylline added.

Figure 6:
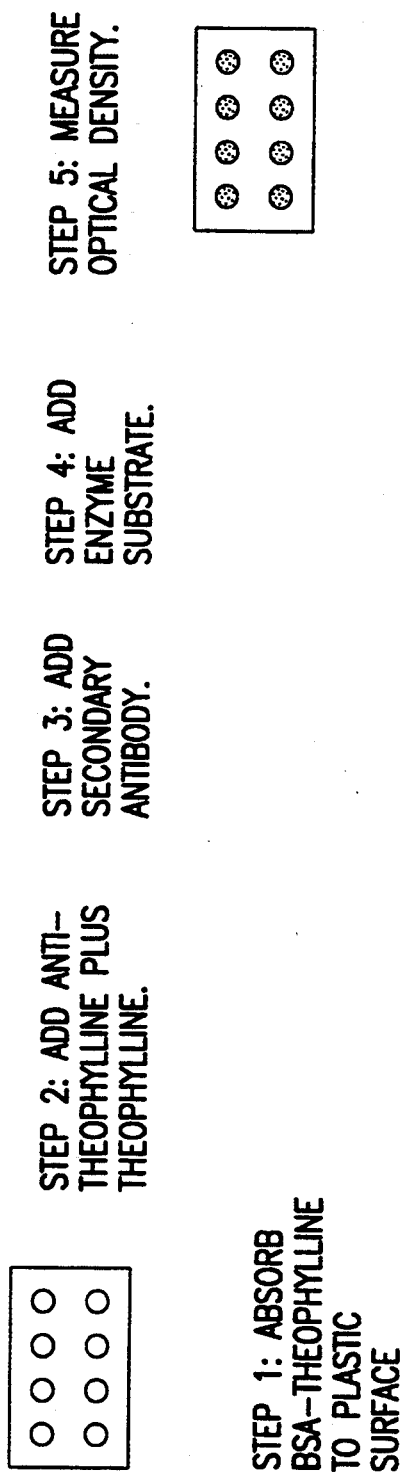
FIG. 6 is a schematic diagram comparing the steps of an enzyme-linked immunosorbant assay to an immunosorbant assay of the present invention.
Figure 6:

Cuvettes and microtiter plates were incubated with theophylline-BSA for 1 hour, washed three times, and then incubated for 1 hr with a buffer solution containing 1% BSA to block any sites on the polystyrene which were not covered with protein. In the LISA, after washing out the blocking solution, solutions of antitheophylline liposomes and theophylline were added to the cuvettes. After 30 min. incubation, unbound antitheophylline liposomes were washed out of the cuvettes. Bound liposomes were solubilized with a detergent solution, and their associated fluorescence was measured at 520 nm by exciting samples at 490 nm. In the ELISA, the wash step which followed blocking was then followed by the addition of antitheophylline plus theophylline. After 60 min., unbound antitheophylline was washed out. This was followed by the addition of peroxidase-labeled secondary antibody (peroxidase antimouse antibody), which served as an indicator of the presence of antitheophylline bound to immobilized theophylline. After an additional 60 min. incubation, the peroxidase-antibody which did not bind to the antitheophylline was washed out. This step was then followed by an additional step: incubation with peroxidase substrate, 2,2'-Azinobis(3-ethylbenzthiazolinesulfonic acid). After 30 min additional incubation, the reaction was stopped by addition of sodium azide to each well. The optical density of each well at 414 nm was measured in an ELISA plate reader. The two assays are compared schematically in FIG. 6.

Almost all aspects of the two assays, such as incubation times at common steps, and concentrations of reagents, were identical. The concentration of antitheophylline used for ELISA was twice the molar concentration of liposomes used in LISA. The ELISA was performed in microtiter plates in a volume of 0.1 ml and the LISA in polystyrene cuvettes with a reaction volume of 0.5 ml and a final volume of 2 ml. From the BSA blocking step to completion, the LISA took approximately 40 min, and the ELISA took about 3.5 hr.

Figure 7:
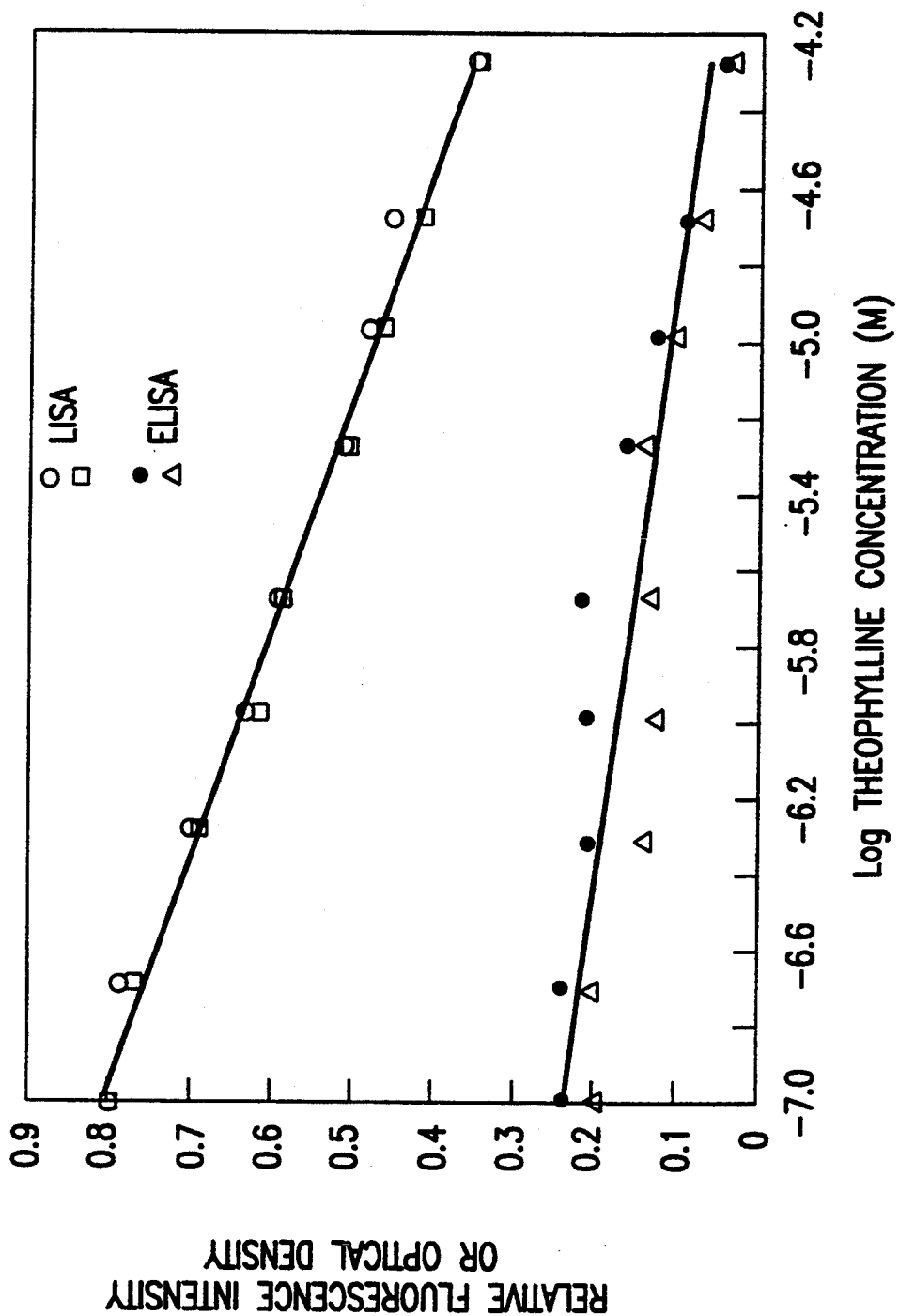
FIG. 7 is a graph which shows a comparison between the relationship of relative fluorescence intensity and the log of theophylline concentration of an immunosorbant assay of the present invention and an enzyme-linked immunosorbant assay.

The results of the comparative assays are shown in FIG. 7. The two assays provided qualitatively similar results, but the LISA assay was more sensitive due to increased precision and a greater change in signal with change in concentration. Statistical analysis showed that LISA is at least two orders of magnitude more sensitive than the corresponding ELISA.

In a different embodiment of the present invention, the intensity of scattered light was quantitated as a measure of liposome aggregation in response to a concentration-dependent immunospecific reaction. Liposome aggregation experiments were performed in a spectrofluorimeter using a 450 watt xenon light source by monitoring the intensity of 500 nm light scattered 90° to incident. Liposomes were allowed to incubate for 3 min with avidin before addition of B-Ab. For all experiments, liposomes were present at a concentration of 0.5 nmol total lipid in 2.5 ml, and were continuously stirred.

All solutions were prepared in aqueous buffer (TBS) containing 0.02M Tris, 0.15M NaCl, and 0.01% (w/v) NaN$_3$ (pH 7.4).

Figure 8:
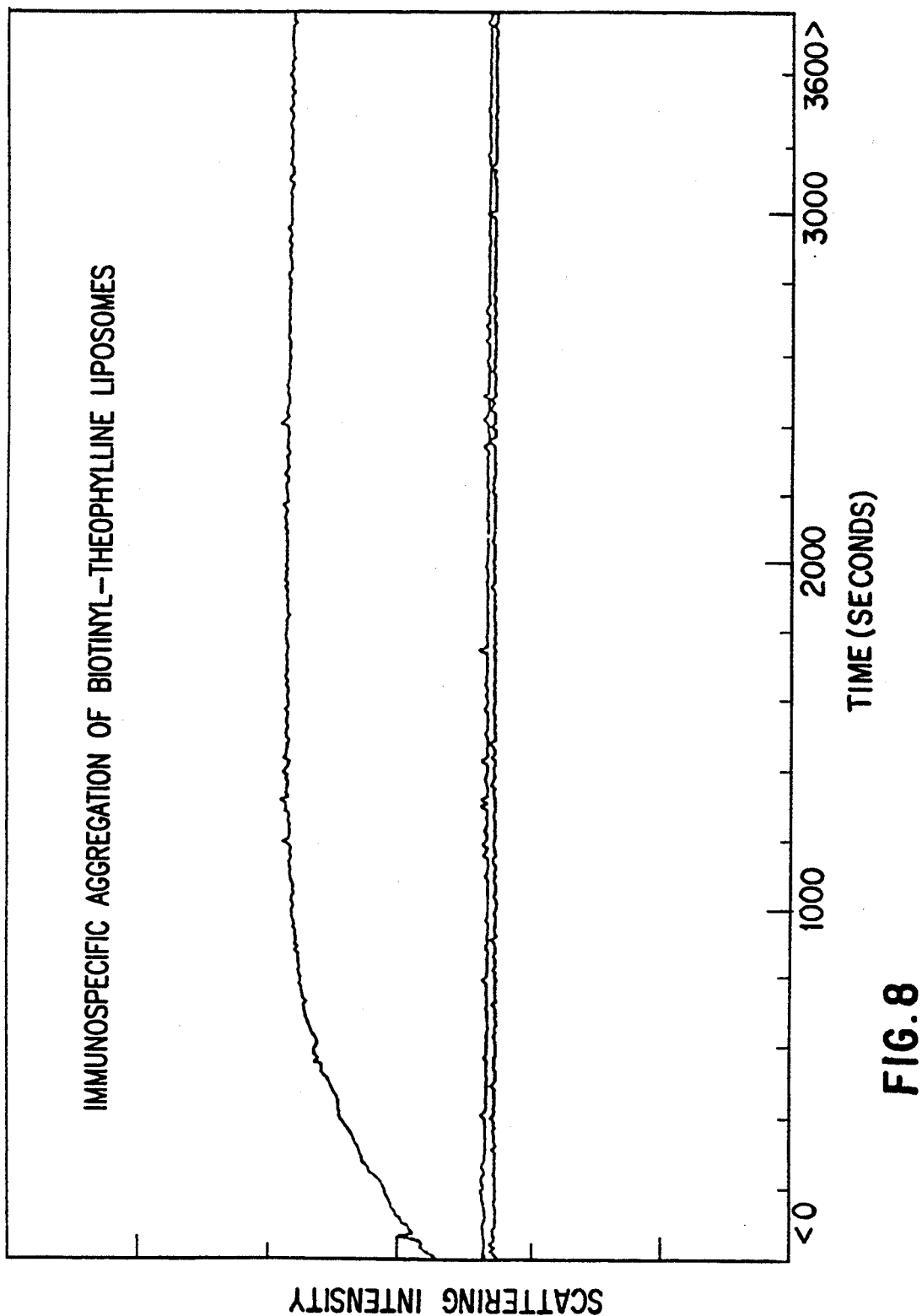
FIG. 8 is a graph showing the immunospecific aggregation of liposomes in relation to time.
Figure 9:
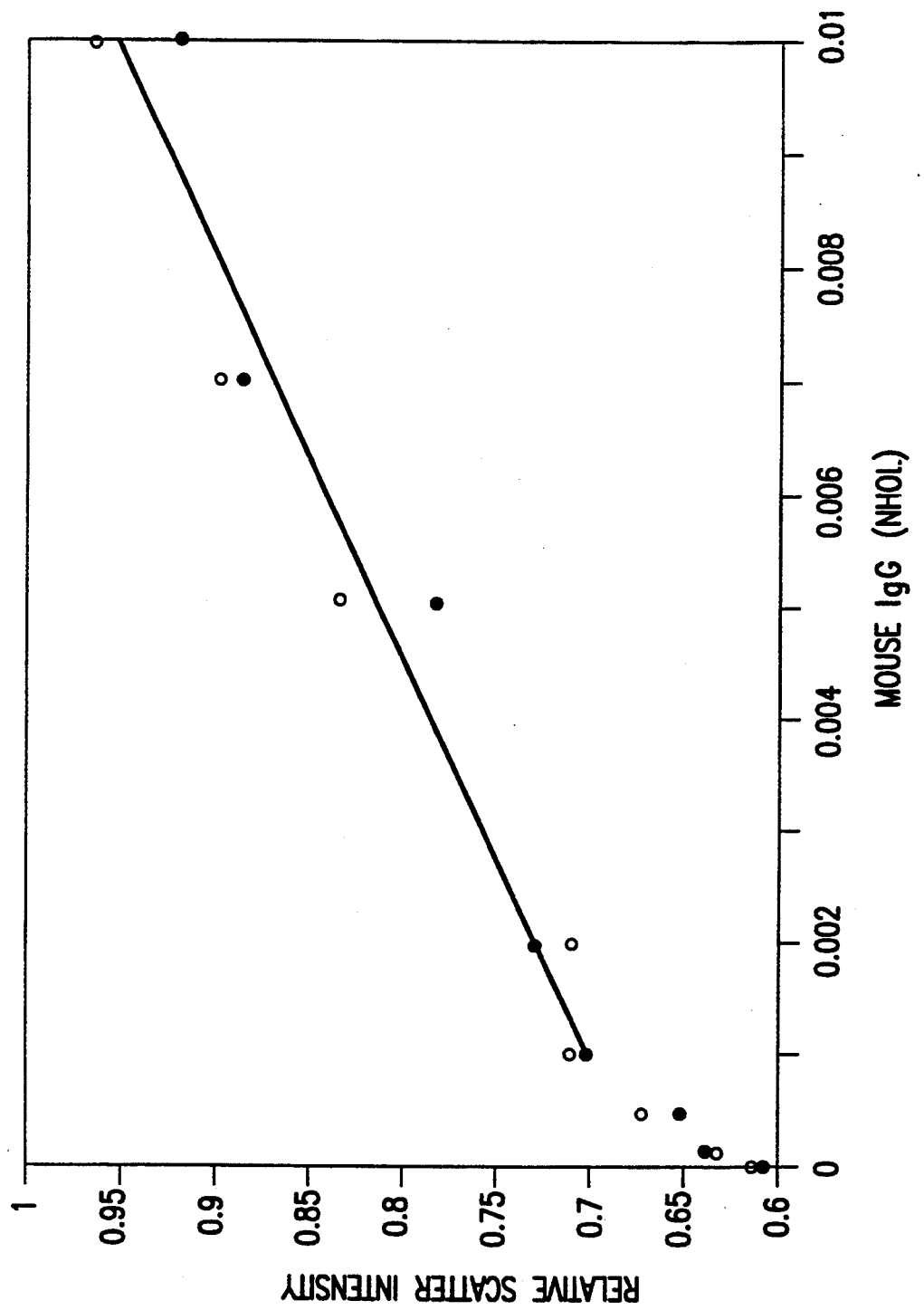
FIG. 9 is a graph showing the relative scatter intensity of light in relation to the concentration of mouse IgG when tested in accordance with an embodiment of the present invention.

The immunospecific reactivity of liposomes non-covalently derivatized with B-Ab was examined by measuring changes in intensity of scattered light as liposomes aggregated in the presence of multivalent antigen. Immunospecific aggregation data are shown in FIGS. 8 and 9. FIG. 8 shows that the amount of aggregation induced by the presence of antibody in 10 l of ascites fluid increased as the molar ratio of B-PE in liposomes increased, although significant non-specific aggregation occurred above 0.5% mol % B-PE. In FIG. 9, increasing amounts of B-Ab were added to 0.1 mol % B-PE liposomes which were first incubated with 0.4 nmol of avidin. Immunospecific aggregation continued to increase even at a molar ratio of B-Ab to avidin of 3.5.

Based on the above data, an optimized formulation was chosen for measuring a concentration-dependent immunospecific response. Liposomes were prepared containing 0.1 mol % B-PE, since this preparation seemed adequately resistant to nonspecific aggregation. Avidin was added to a small volume of liposomes at a concentration to provide a B-PE:avidin molar ratio of 5, and after 2 min, B-Ab was added at a B-Ab:avidin molar ratio of 3. After 10 min, varying amounts of purified mouse IgG were added. Samples were allowed to react at room temperature for 1 hr., at which time they were diluted with 2 ml TBS. The calibration curve is shown in FIG. 9. Scatter intensity increased linearly as a function of IgG concentration between 1 and 10 pmol IgG. The curve was nonlinear above and below these concentrations.

In another embodiment of the present invention, a sample kit for qualitatively testing the presence of an analyte in a sample is provided. The kit comprises a capillary tube or receptor cartridge having immobilized receptor packed therein. The receptor may be an antibody or antigen analog or the like. A mixture is formed by adding a sample to be tested for presence of an analyte to liposomes each having a surface membrane and an interior aqueous phase, the surface membrane having a binding agent incorporated therein, the aqueous phase including a color dye. The capillary tube is inserted, preferably vertically, into the mixture, and through capillary action, mixture is drawn upward within the capillary tube. Detection of bound liposomes can be enhanced by blotting the capillary tube onto absorbent material to absorb the aqueous phase and thus concentrate the dye on the absorbent material leaving a color spot to facilitate detection. The liposomes and the analyte compete for binding to the receptor. The resulting color intensity of the tube or the absorbent material is indicative of the presence of analyte in the sample, greater color intensity indicating greater liposome binding and therefore lower analyte concentration. The immobilized receptor cartridge can be reusable after disrupting liposomes and washing out reactants.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. A flow injection immunoassay method for detecting or quantifying an analyte in a test sample, said method comprising:
   (a) providing a stationary solid phase support having bonded thereto a receptor for competitively binding thereto said analyte and sensitized liposomes;
   (b) forming said sensitized liposomes having a surface membrane and an interior aqueous phase, said surface membrane having a binding agent incorporated thereinto that binds to said receptor in competition with said analyte and said liposomes including a marker compound, wherein said sensitized liposomes will not disrupt as a result of any bonding between said binding agent and said receptor;
   (c) flowing a sample which may contain said analyte past said solid phase support in a moving, non-segmented carrier stream;
   (d) flowing said liposomes past said solid phase support in said stream, whereby flow separates liposomes bound to said solid phase support from liposomes unbound to said solid phase support; and
   (e) detecting said marker compound or a reaction product of said marker compound of either the bound liposomes or the unbound liposomes to determine the presence or amount of analyte in said test sample.

2. A flow injection immunoassay method for detecting or quantifying an analyte in a test sample, said method comprising:
   (a) providing a stationary solid phase support having bonded thereto a receptor for only one of said analyte and sensitized liposomes;
   (b) forming said sensitized liposomes having a surface membrane and an interior aqueous phase, said surface membrane having a binding agent incorporated thereinto that binds to at least one of said receptor and said analyte and said liposomes including a marker compound, wherein said sensitized liposomes will not disrupt as a result of any bonding between said binding agent and said receptor or said binding agent and said analyte;
   (c) flowing a sample which may contain said analyte past said solid phase support in moving, non-segmented carrier stream;
   (d) flowing said liposomes past said solid phase support in said stream, whereby flow separates liposomes bound to said solid phase support from liposomes unbound to said solid phase support; and
   (e) detecting said marker compound or a reaction product of said marker compound of either the bound liposomes or the unbound liposomes to determine the presence or amount of analyte in said test sample.

3. The immunoassay of claim 1, wherein said liposomes are sensitized with binding agents via a noncovalent bridge between biotinyl liposomal lipid and biotinyl binding agent with the protein avidin.

4. The immunoassay of claim 1, wherein said marker compound comprises unquenched fluorophores which are detected while within said interior phase of said bound or unbound liposomes.

5. The immunoassay of claim 1, wherein said marker compound is an electroactive marker.

6. The immunoassay of claim 1, wherein said marker compound is an enzyme and an enzyme reaction product is detected.

7. The immunoassay of claim 1, wherein said marker compound is a dye.

8. The immunoassay of claim 2, wherein said sensitized liposomes and said sample are flowed past said solid phase support at a controlled flow rate of said sensitized liposomes and said sample.

9. The immunoassay of claim 8, wherein said controlled flow rate is about 5 ml/min.

10. The immunoassay of claim 2, wherein said sample is injected into a straight sample loop and said liposomes are injected into a sample loop which is knotted or coiled to induce mixing.

11. The immunoassay of claim 2, wherein said sample is mixed with a buffered reagent prior to injection of said sample into an immunoreactor.

12. The immunoassay of claim 2, wherein microprocessor-controlled valves deliver said samples and said liposomes to the solid phase support.

13. The immunoassay of claim 2, wherein a continuously flowing aqueous stream carries unbound liposomes and unreacted sample away from the solid phase support.

14. The immunoassay of claim 2, wherein regenerating reagent is automatically applied to said solid phase support to disrupt liposomes for regeneration of receptor sites for reuse after step (d).

15. The immunoassay of claim 2, wherein a continuously flowing aqueous stream carries said marker compound to a means for detecting the presence or the concentration of said marker compound.

16. The immunoassay of claim 2, wherein said marker compound is an electroactive marker.

17. The immunoassay of claim 2, wherein said marker compound is an enzyme, and an enzyme reaction product is detected.

18. The immunoassay of claim 2, wherein said marker compound is a dye.

19. The immunoassay of claim 2, wherein said binding agent is selected from the group consisting of antigens, antibodies and antibody fragments.

20. The immunoassay of claim 10, wherein said marker compounds are selected from the group consisting of unquenched fluorophores and dyes.

21. The immunoassay of claim 1, wherein step (e) comprises detecting marker compounds or reaction products thereof by disrupting liposomes remaining bound to the solid phase support after flowing both said liposomes and said sample past said solid phase support.

22. The immunoassay of claim 1, wherein step (e) comprises detecting marker compounds or reaction products thereof by disrupting liposomes which do not remain bound to said solid phase support after flowing both said liposomes and said sample past said solid phase support.

23. The immunoassay of claim 1, wherein step (e) comprises detecting marker compounds while said marker compounds are in undisrupted liposomes bound or not bound to said solid phase support after flowing both said liposomes and said sample past said solid phase support.

24. The immunoassay of claim 2, wherein step (e) comprises detecting marker compounds or reaction products thereof by disrupting liposomes remaining bound to the solid phase support after flowing both said liposomes and said sample past said solid phase support.

25. The immunoassay of claim 2, wherein step (e) comprises detecting marker compounds or reaction products thereof by disrupting liposomes which do not remain bound to said solid phase support after flowing both said liposomes and said sample past said solid phase support.

26. The immunoassay of claim 2, wherein step (e) comprises detecting marker compounds while said marker compounds are in undisrupted liposomes bound or not bound to said solid phase support after flowing both said liposomes and said sample past said solid phase support.

27. The immunoassay of claim 2, wherein said binding agent binds to said receptor and said analyte.

28. The immunoassay of claim 2, wherein said receptor and said binding agent bind to said analyte.

* * * * *